United States Patent [19]

Burton et al.

[11] Patent Number: 5,580,023

[45] Date of Patent: Dec. 3, 1996

[54] INTEGRATED OPHTHALMIC EXAMINATION CHAIR AND POSITIONING SYSTEM

[75] Inventors: Roy H. Burton, Columbus; David E. Wood, Grove City; Kevin W. Intrieri, Dublin, all of Ohio

[73] Assignee: R. H. Burton Company, Grove City, Ohio

[21] Appl. No.: 444,004

[22] Filed: May 18, 1995

Related U.S. Application Data

[63] Continuation-in-part of Ser. No. 287,155, Aug. 8, 1994.

[51] Int. Cl.⁶ .................................................. F16M 13/00
[52] U.S. Cl. .................................... 248/430; 297/344.14
[58] Field of Search .................................. 248/429, 424, 248/430; 297/344.14, 344.13, 344.11, DIG. 4

[56] References Cited

U.S. PATENT DOCUMENTS

| | | | |
|---|---|---|---|
| 2,553,652 | 5/1951 | Gradle | 248/430 |
| 3,259,355 | 7/1966 | Slouka | 248/430 |
| 3,392,954 | 7/1968 | Malitte | 248/429 |
| 3,741,513 | 6/1973 | Wilson | 248/429 |
| 3,806,191 | 4/1974 | Stegmaier | 248/429 X |
| 4,741,506 | 5/1988 | Schwaegerle | 248/430 |
| 4,768,831 | 9/1988 | Liedberg | 297/344.14 X |
| 5,029,941 | 7/1991 | Twisselmann | 297/344.13 X |
| 5,195,712 | 3/1993 | Goodall | 248/429 X |

*Primary Examiner*—J. Franklin Foss
*Attorney, Agent, or Firm*—Mueller and Smith, LPA

[57] ABSTRACT

An ophthalmic examination chair having an integrated positioning capability for providing wheel chair access to an associated instrument stand accommodating the examining of disabled patients. The chair has a seat member which is configured to receive a seated patient and is movable from a forward position spacing the seated patient at a predetermined distance from an eye examination target. A lower base member is provided as extending along a longitudinal axis between a forward end and a rearward end, and as having an upper and a lower surface. An upper carriage member, having a bottom surface and a top surface supporting the seat member thereon, is supported on the upper surface of the base member for movement between the forward and the rearward end thereof along the longitudinal axis to position the seat member at the forward position and at a rearward position providing access to the instrument stand by a wheel chair patient positioned at the predetermined distance from the eye examination target. A locking assembly is employed to releasably lock the carriage member in a forward orientation disposing the examination chair at the forward position, and in a rearward orientation disposing the examination chair at the rearward position.

23 Claims, 6 Drawing Sheets

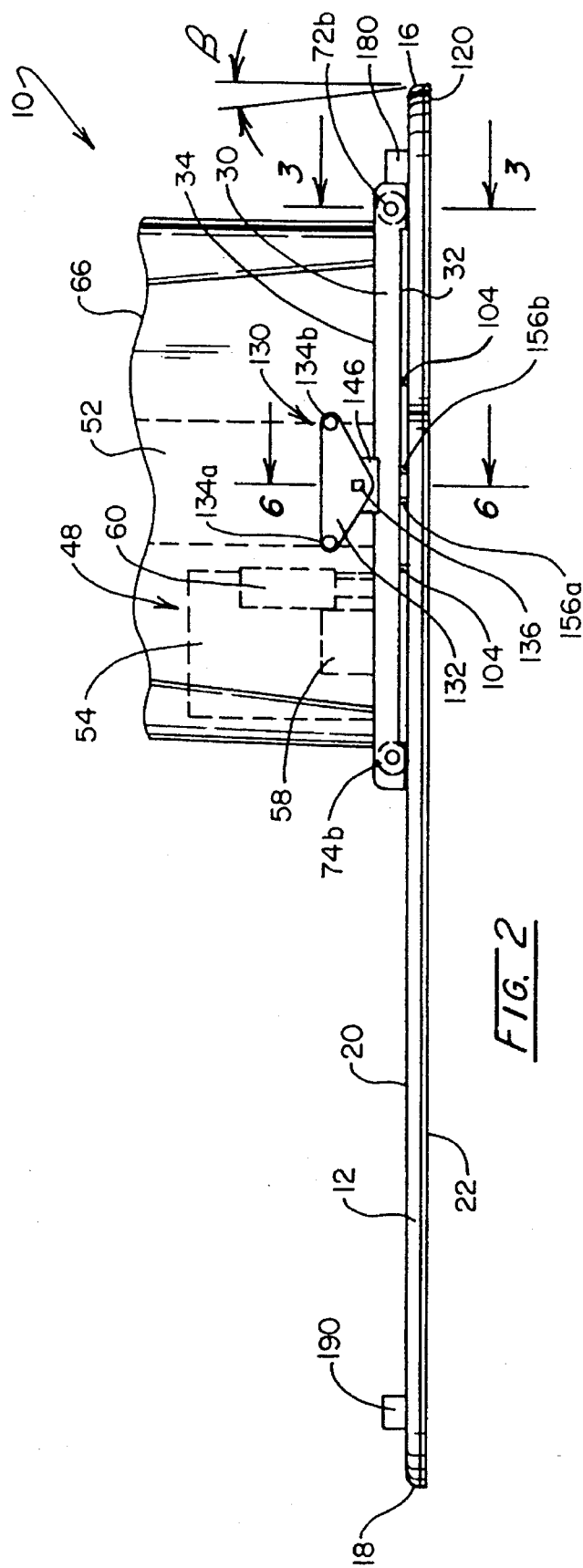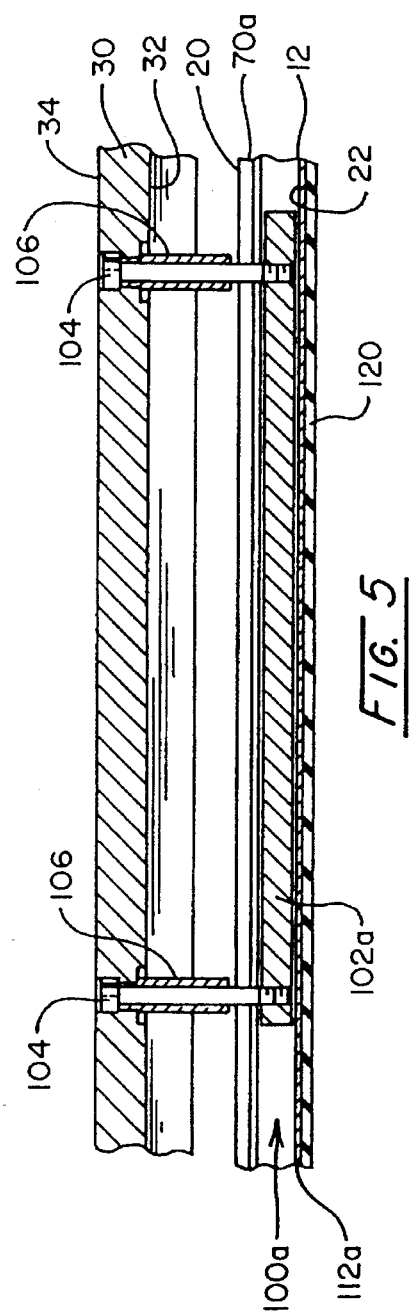

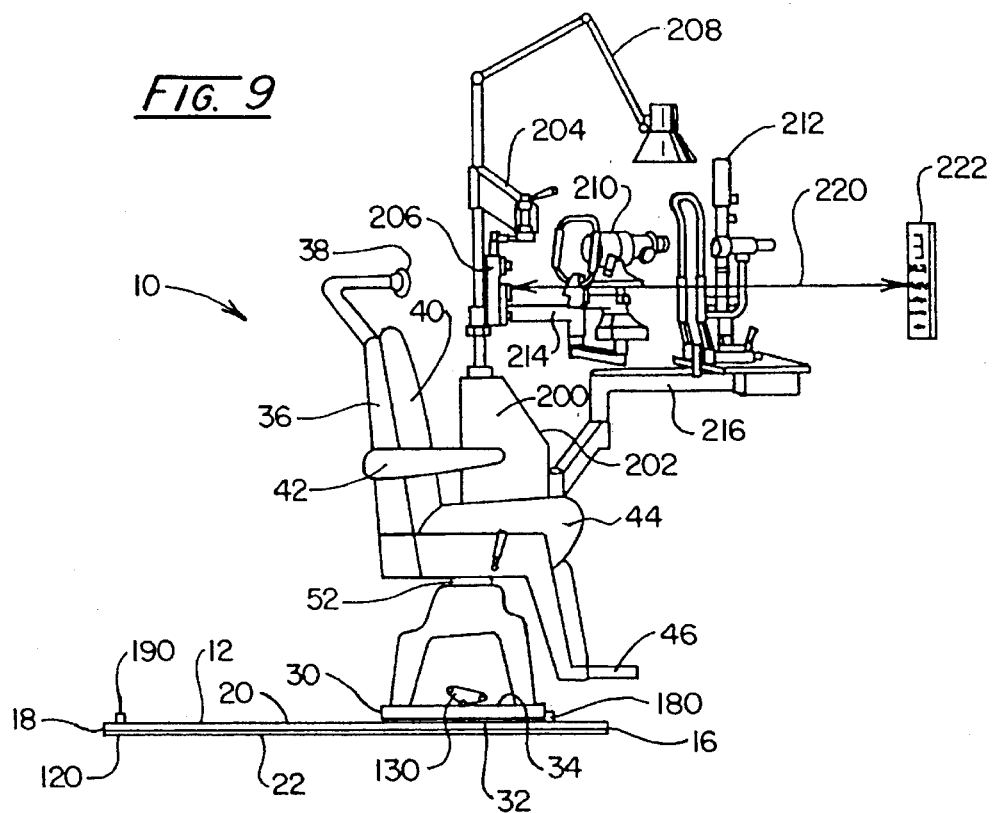
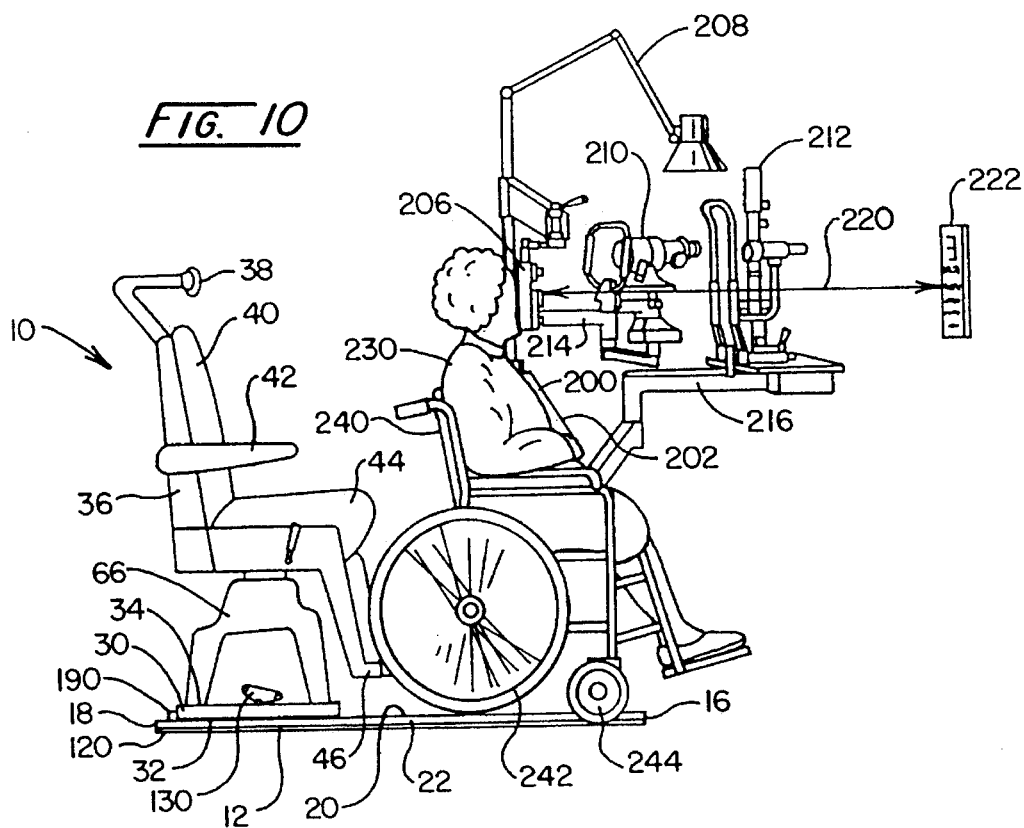

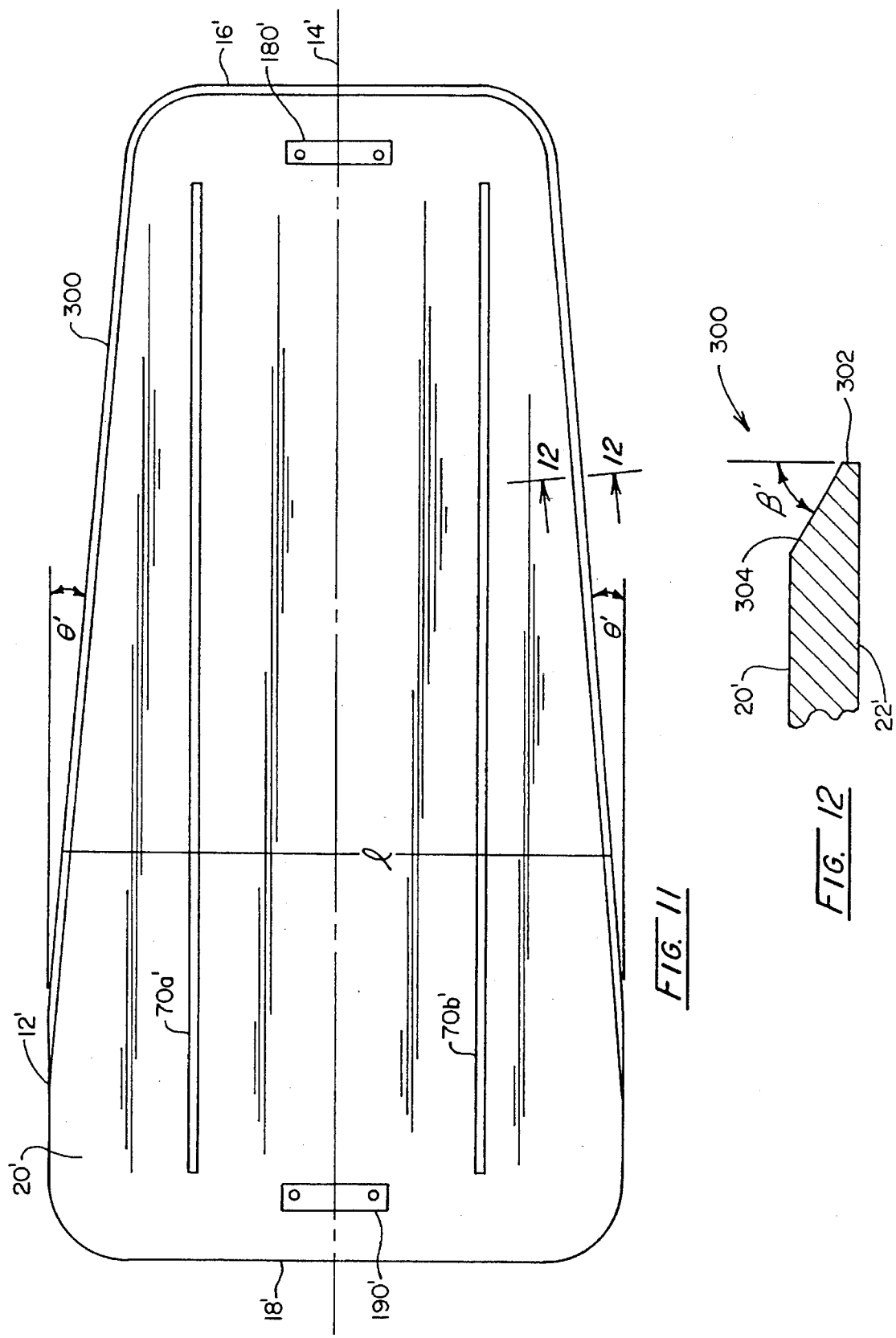

INTEGRATED OPHTHALMIC EXAMINATION CHAIR AND POSITIONING SYSTEM

CROSS-REFERENCE TO RELATED APPLICATION

This application is a continuation-in-part of U.S. application Ser. No. 08/287,155, filed Aug. 8, 1994, and entitled "Ophthalmic Examination Chair Positioning System," the disclosure of which is expressly incorporated herein by reference.

BACKGROUND OF THE INVENTION

The present invention relates generally to an ophthalmic examination chair having integrated positioning system providing wheel chair access to an associated instrument stand for accommodating the examination of disabled patients.

Nineteen ninety two heralded the passage of the Americans with Disabilities Act (ADA) which extended the protection of the federal civil rights laws to disabled Americans in such areas as employment, public accommodations, state and local government services, public and private transportation, and telecommunication services. In particular, Title II of the ADA, which applies to all private entities that own, operate, or lease a "place of public accommodation," prohibits such entities from discriminating against the disabled. Specifically, the ADA requires each and every "place of public accommodation" to insure that no individual with a disability is excluded, denied services, segregated, or generally treated differently from other individuals because of the absence of auxiliary aids and services adapted to accommodate the disability. Penalties for violations of the ADA include monetary fines as high as fifty thousand dollars for the first infraction and one hundred thousand dollars for subsequent infractions, as well as temporary or permanent injunctive orders requiring the altering of facilities to prohibit continuing discrimination. A tax credit, however, has been made available for "eligible access expenditures" to help mitigate the expense of modifying or acquiring equipment or devices for providing goods and services to the disabled.

Although the passage of the ADA generally has been praised as rightly affording the over 40 million disabled Americans equal access to all public places, compliance with the provisions of the act often has proven to be both costly and difficult for many industries, businesses, and services. The medical professions too have been confronted with the problem of how to comply with the requirements of the ADA. Indeed, ensuring that the disabled have unrestricted access to needed medical care may be seen as a motivating factor behind the passage of the ADA.

As with all health care providers, the providers of ophthalmic and optometric services, such as ophthalmologists, optometrists, opticians, and the like have been exploring various ways of meeting their obligation of reasonable accommodation under the ADA. As usually equipped, the standard ophthalmic examination room involves an instrument stand having a movable arm supporting a refractor assembly, which assembly contains a number of adjustable testing lenses and, optionally, other eye examination instruments such as a keratometer and a slit lamp. The stand additionally may support a holder for such hand-held diagnostic instruments as an ophthalmoscope and a retinoscope. An examination chair is associated with the stand and is positioned with respect thereto such that refractor assembly may be placed confronting the eyes of the patient being examined. With the patient and the refractor assembly properly positioned, the examination procedure commences with the darkening of the examination room, and the observing by the patient of a distant target, such as an eye chart or the like, through the lenses of the refractor assembly. The examination chair is positioned to space the patient a predetermined distance from the eye chart which is calibrated to be read from a specified distance by the patient. The lenses of the refractor assembly then are adjusted using a trial-and-error procedure until the desired degree of vision correction is obtained. As the trial-and-error procedure may become somewhat involved and protracted, the comfort of both the patient and the examiner is of great importance. Accordingly, most examination chairs are designed to be adjustable as to height or degree of incline via an internally-contained pneumatic, mechanical, or electrical arrangement. Such an arrangement, however, adds to weight of the chair which may weigh several hundred pounds unloaded.

Given the weight of the examination chair and the need for it to be positioned in close adjacency to the instrument stand and at a predetermined distance from the eye chart, it generally is considered to be neither movable or portable once placed within the examination room. This poses difficulties for the provider where wheel chair bound patients are the subject of treatment. Indeed, the only options heretofore available for providers seeking to comply with the ADA requirements have been either to physically transfer the patient from the wheel chair to the examination chair, or to establish a separate examining room for wheel-chair-bound patients. A significant risk of personal injury, however, both to the patient and to the person or persons assisting the patient, attends the physical transferring of the patient out of the wheel chair and into the examination chair. With such risks of injury comes an increased liability to the provider. Moreover, many providers have neither the office space nor the funds necessary to establish a separate examining room and to equip it with specialized chairs and instrument stands specifically designed to accommodate the disabled. Accordingly, it will be appreciated that other, less-expensive alternatives for providers of eye care to conform to the provisions of the ADA would be welcomed by all of those involved. Especially desired would be an examination chair having an inherent capability to accommodate both ambulatory and wheel-chair bound patients.

BROAD STATEMENT OF THE INVENTION

The present invention is directed to an ophthalmic examination chair having an integrated positioning capability for providing wheel chair access to an instrument stand accommodating the examining of disabled patients. In providing the examination chair as having a lower base member and m tipper carriage member supported for movement along the base member, the present invention allows for the facile repositioning of the seat member of the chair from a forward position for spacing a seated patient a predetermined distance from an eye examination target, to a rearward position for providing access to the instrument stand by a patient in the wheel chair.

One aspect of the invention therefore involves an ophthalmic examination chair for use in conjunction with an associated instrument stand and eye examination target. The chair has a seat member which is configured to receive a seated patient and is movable from a forward position spacing the seated patient at a predetermined distance from the eye examination target. A lower base member is provided as extending along a longitudinal axis between a forward end and a rearward end, and as having an tipper and a lower surface. An upper carriage member, having a bottom surface and a top surface supporting the seat member thereon, is supported on the upper surface of the base member for movement between the forward and the rearward end thereof along the longitudinal axis to position the seat member at the forward position and at a rearward position providing access to the instrument stand by a patient in a wheel chair positioned at the predetermined distance from the eye examination target. A locking assembly is employed to releasably lock the carriage member in a forward orientation disposing the examination chair at the forward position, and in a rearward orientation disposing the examination chair at the rearward position.

A further aspect of the present invention involves a method of providing access by patient in a wheel chair to an ophthalmic instrument stand having an associated examination chair and eye examination target. The examination chair is provided as having a seat member which is configured to receive a seated patient and is movable from a forward position spacing the seated patient at a predetermined distance from the eye examination target. A lower base member is provided as extending along a longitudinal axis between a forward end and a rearward end, and as having an upper and a lower surface. An upper carriage member, having a bottom surface and a top surface supporting the seat member thereon, is supported on the upper surface of the base member for movement between the forward and the rearward end thereof along the longitudinal axis to position the seat member at the forward position and at a rearward position providing access to the instrument stand by the patient in the wheel chair. The carriage member of the examination chair is moved rearwardly along the longitudinal axis of the base member to move the seat member from the forward position to the rearward position. The wheel chair then is moved rearwardly over tile base member, and the wheel chair is positioned to space the patient therein at the predetermined distance from the eye examination target.

Advantages of the present invention include an ophthalmic examination chair having an integrated positioning capability providing efficient wheel chair access to an associated instrument stand in a minimum amount of space which is generally available in any examination room without the reconfiguration thereof. In allowing the disabled patient to remain seated in his or her wheel chair, the system also assures the dignity of the patient while eliminating the risk of personal injury which attends the removal of the patient from the wheel chair. Additional advantages of the present invention include the provision of a stable but movable examination chair having a low profile minimizing the hazard to ambulatory patients stepping down from the examination chair while under debilitating medications such as anesthetics or eye dilation drops. Further advantages include an examination chair which may be moved with minimal effort, but which is lockable and self-positioning to return the examination chair to a calibrated forward position spaced a predetermined distance from an eye examination target. The chair additionally may be configured to automatically position the wheel chair at the same calibrated, predetermined position. Still further advantages includes a chair which allows providers to inexpensively conform to ADA requirements. These and other advantages will become readily apparent to those skilled in the art based upon the disclosure contained herein.

BRIEF DESCRIPTION OF THE DRAWINGS

For a fuller understanding of the nature and objects of the invention, reference should be ha to the following detailed description taken in connection with the accompanying drawings wherein:

FIG. 2 is a partial side view of the examination chair of FIG. 1;

FIG. 5 is a cross-sectional view taken through line 5—5 of FIG. 1 showing in enhanced detail a guide bar assembly of the examination chair of FIG. 1;

FIG. 9 is a schematic view illustrating the examination chair of the present invention as having an associated instrument stand and disposed at a forward position for spacing a seated at a predetermined distance from an eye examination target;

FIG. 10 is a schematic view of the examination chair of FIG. 9 shown as disposed at a rearward position providing access to the instrument stand by a patient in a wheel chair;

FIG. 11 is a top view of an alternative embodiment of the lower base member of the integrated examination chair and positioning system of FIG. 1; and FIG. 12 is a cross-sectional view taken through line 12—12 of FIG. 11 showing the top surface of the lower base member of FIG. 12 as having a rearwardly inclined periphery.

The drawings will be described further in connection with the following Detailed Description of the Invention.

DETAILED DESCRIPTION OF THE INVENTION

Figure 1:
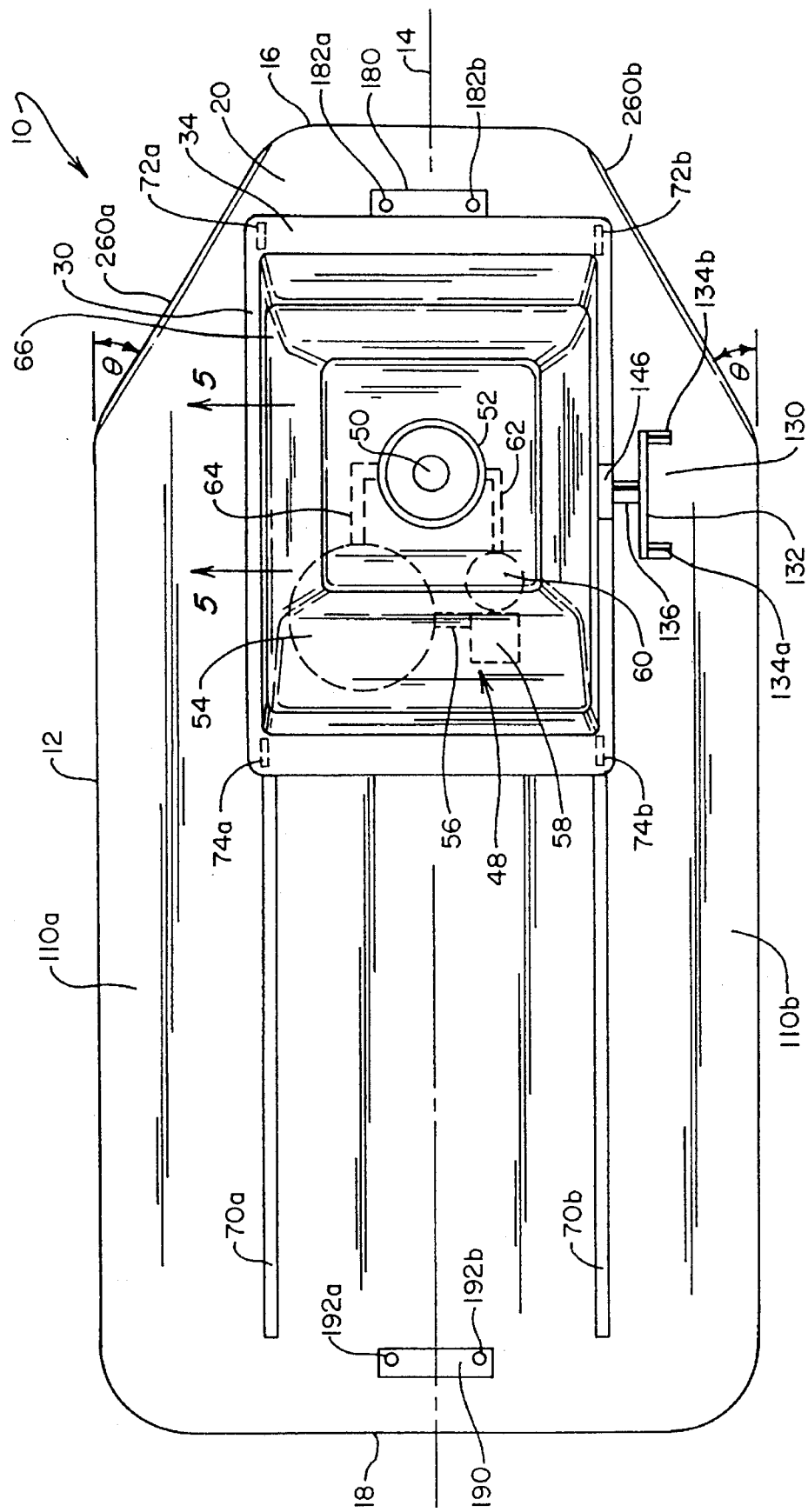
FIG. 1 is a top view of the integrated examination chair and positioning system of the present invention shown with the seat member thereof removed to reveal the details of its inner construction including a lower base member, a movable upper carriage, and a locking assembly.

Referring to the figures wherein like parts are designated with like reference numerals, and initially to FIGS. 1–2, shown generally at 10 is an ophthalmic examination chair. In accordance with the present invention, chair 10 is provided as having an integrated positioning capability for moving the seat member thereof between a forward position spacing a seated patient a predetermined distance from an eye examination target and a rearward position providing access to an associated instrument stand by a patient in a wheel chair. For illustrative purposes, chair 10 is depicted in FIGS. 1 and 2 with the seat or bucket portion thereof removed to reveal the details of its inner construction. In this regard, chair 10 may be seen to include a lower base member, 12, extending along a longitudinal axis, 14 (FIG. 1), between a forward end, 16, and a rearward end, 18, and having an upper surface, 20, and a lower surface 22 (FIG. 2). It will be appreciated in view of the disclosure to follow hereinafter that base member 12 is adapted to receive the 20 inch (51 cm) to 22 inch (56 cm)

rear wheel spans of most wheel chairs thereon in having a preferred widthwise extent of about 22.5 inches (57.15 cm). Base member 12 preferably is formed of a mild steel for stability and strength considerations.

Supported on the upper surface 20 of base member 12 is an upper carriage member, 30, having a bottom surface, 32 (FIG. 2), and an oppositely-disposed top surface, 34, for supporting the seat member of chair 10 thereon. Looking momentarily to FIGS. 9 and 10, such seat member is shown at 36 as being configured to receive a seated patient (not shown) in having a head supporting portion, 38, a back supporting portion, 40, an arm supporting portion, 42, a seat supporting portion, 44, and a foot supporting portion, 46. As the combined weight of seat member 36 and any patient seated therein may exceed 500 lbs (225 kg), it is preferred that the lower surface 32 of carriage member 30 be cast of a mild steel and reinforced with all integrally-formed, rib-type infrastructure (not shown).

Returning to FIGS. 1 and 2, top surface 34 of carriage member 30 preferably is provided as having minimum widthwise by lengthwise plan dimensions of 12.65 inches (32.13 cm) by 19.4 inches (49.28 cm) to accommodate a standard actuating assembly, shown mostly in phantom at 48, for effecting the raising and lowering seat member 36 (FIGS. 9 and 10) to various height positions. As is typical for most standard ophthalmic examination chairs, actuating assembly 48 includes for connection to seat member 36 a post or ram, 50, driven along a generally vertical travel by a hydraulic cylinder, 52, which may be of single-acting, bi-directional, gravity return type. Cylinder 52 is actuated with hydraulic fluid supplied by an electric pump, 54, having a self-contained fluid reservoir and being coupled in fluid communication via line 56 to a flow control valve, 58, having an associated gauge, 60. Valve 58 is coupled in fluid communication via inlet or feed line 62 with cylinder 52 which, in turn, is coupled with pump 54 via outlet or return line 64 to complete the hydraulic circuit. A generally pyramidal-shaped housing, 66, is provided to enclose actuating assembly 48.

Carriage member 30 is supported on base member 12 for movement between forward and rearward ends 16 and 18 thereof along longitudinal axis 14. Such movement will be appreciated to effect the positioning of the seat member 36 (FIGS. 9 and 10) of examination chair 10 between the forward position spacing a seated patient a predetermined distance from an eye examination target, as is shown in FIGS. 9, and a rearward position providing wheel chair access to the associated instrument stand, as is shown in FIG. 10. With the lengthwise dimension of base member 12 selected as being about 45 inches (114.3 cm), carriage member 30 is provided with a uniaxial travel distance of about 20 inches (50.8 cm). Such travel distance is sufficient to allow wheel chair access to the instrument stand associated with examination chair 10, but is not so long as to require the reconfiguration of the typical examination room to provide more space behind the examination chair than is normally available.

Preferably, and as may be seen in FIG. 1, base member upper surface 20 is integrally formed as including a pair of spaced-apart guide slots, 70a and 70b, extending intermediate forward and rearward ends 16 and 18 thereof generally parallel to longitudinal axis 14. For travel along slots 70, at least one and, preferably, two pairs of guide rollers, 72a–b and 74a–b, are mounted to the bottom surface 32 of carriage member 30. Each of guide rollers 72 and 74 is received in a corresponding one of guide slots 70 for rotation therealong as carriage member 30 is moved along longitudinal axis 14.

Figure 3:
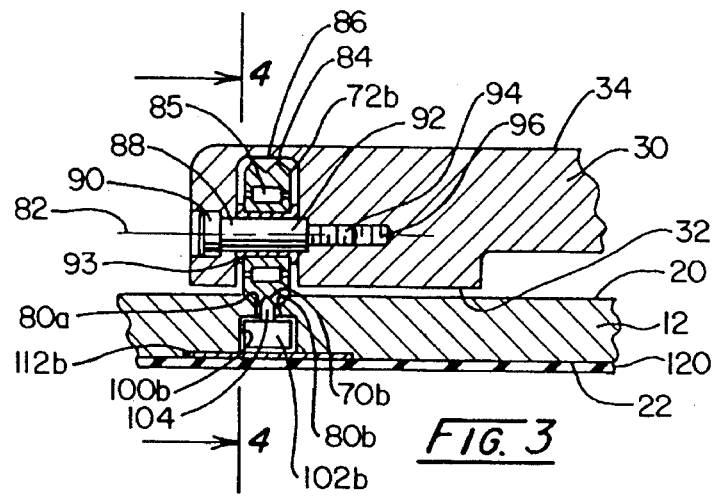
FIG. 3 is a cross-sectional view taken through line 3—3 of FIG. 2 showing in enhanced detail a guide roller assembly of the examination chair of FIG. 1.
Figure 4:
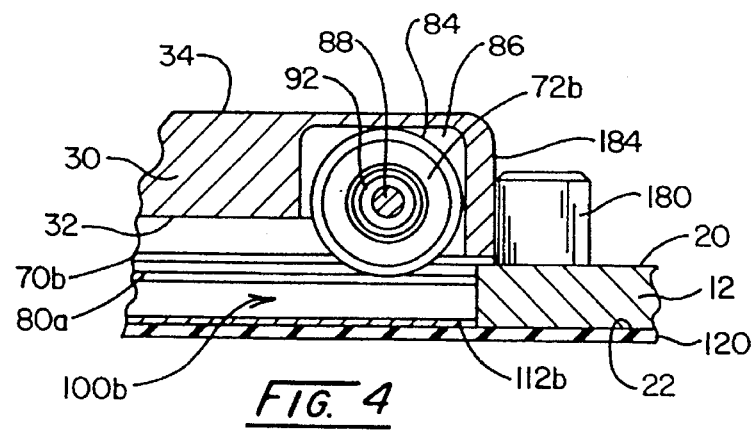
FIG. 4 is a cross-sectional view of the roller assembly of FIG. 3 taken through line 4—4 of FIG. 3.

Referring next to FIGS. 3 and 4, wherein guide roller 72b is shown as received within guide slot 70b, each of guide slots 70 preferably are formed as a pair of inwardly-sloping side surfaces, 80a–b, with each of guide rollers 72 and 74 being vertically mounted to the bottom surface 32 of carriage member 30 as having an axis of rotation, represented at 82 for roller 72b, generally parallel thereto. As is shown at 84 for roller 72b, the outer periphery, of each of rollers 72 and 74 is provided as having a generally V-shaped profile configured to be received on the side surfaces 80 of a corresponding one of guide slots 70. Each of rollers 72 and 74 additionally may be provided, as is shown at 85 for roller 72b, as being of a roller bearing type. In this regard, rollers of such type are manufactured by the Bishop-Wisecarver Corp. under the trade designation WX-2.

The bottom surface 32 of carriage member 30 may be formed as having recesses, one of which is shown at 86, each configured to receive a portion of a corresponding one of rollers 72 and 74 therewithin. To maintain a relatively low profile as between base member 12 and carriage member 30 movably supported thereon, it is preferred that rollers 72 and 74 are received within recesses 86 to provide a minimum nominal clearance of 0.1 inch (0.254 cm) between the bottom surface 32 of carriage 30 and the upper surface 20 of base member 12. With that clearance, and with base member 12 and carriage member 30 being formed as having maximum thicknesses of 0.5 inch (1.27 cm) and 1.05 inch (2.67 cm), respectively, the described assembly may be provided as having a height of only about 1.65 inch (4.19 cm). Such a height minimizes the elevation of seat member 36 (FIGS. 9 and 10) of examination chair 10, and, accordingly, the step from which an ambulatory patient, whose eyes may be dilated or other otherwise unaccommodated, must take to exit the chair.

For rotatably supporting each of rollers 72 and 74 within a recess 80, a corresponding axle, one of which is shown at 88, is provided to extend across each recess 80 from a first end, 90, supported within carriage member 30, to a second end, 92, also supported within carriage portion 30. As is shown at 94, each axle 88, which may be provided as a counterbore, ¼-inch by 1-inch (0.56 cm by 2.54 cm) socket head shoulder screw, extends from second end 92 to a terminal threaded region, 96, fastened within a corresponding threaded aperture formed into carriage member 30. Each roller 72 and 74 is supported intermediate the first and second end 90 and 92 of an axle 88 on a split mount bushing, one of which is shown at 93, which preferably is formed of steel but alternatively may be formed of a polymeric material such as a nylon. With each first and second end 90 and 92 of each axle 88 supported by carriage member 30 as illustrated, each threaded region 94 thereof is advantageously isolated from the shear forces developed by the loading of carriage member 30.

With guide slots 70 and guide rollers 72 and 74 provided as described, and with a standard seat member 36 (FIGS. 9 and 10) and actuating assembly 48 (FIGS. 1 and 2) mounted to carriage member 30, a manual push force of only from about 10 lbs (4.5 kg) to a maximum of about 20 lbs (9 kg) is required to move chair 10 between its forward to rearward positions. Such a relatively minimal push force easily accommodates most health care providers or assistants regardless of the gender or physical strength thereof. Thus, an ease of movement is provided which minimizes the time necessary for the positioning of chair 10.

Figure 7:
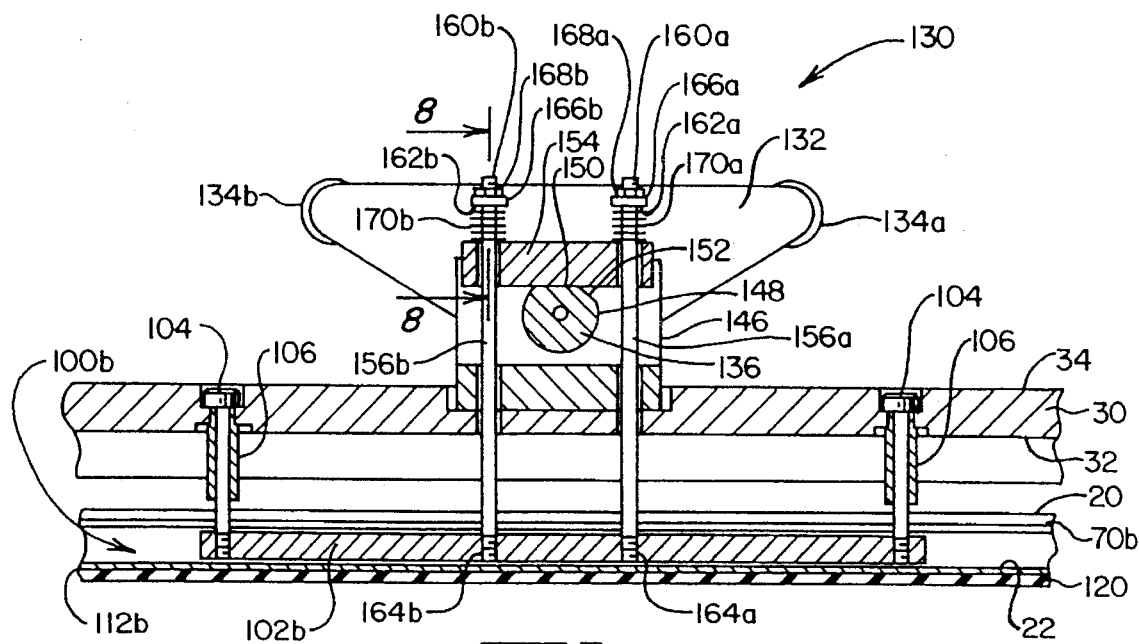
FIG. 7 is a cross-sectional view of the locking assembly of FIG. 6 taken through line 6—6 of FIG. 6.

Looking additionally to FIGS. 5 and 7 in conjunction with FIG. 3, it may be seen that the base member lower surface 22 is formed to include a pair of spaced-apart guide channels, 100a (FIG. 5) and 100b (FIGS. 3 and 7), each extending in registry and open communication with a corresponding one of the guide slots 70. At least a pair of guide members, 102a (FIG. 5) and 102b (FIGS. 3 and 7), are configured to be retained within a corresponding one of guide channels 100. Fox retaining carriage member 30 on base member 12, each guide member 102 is fastened to carriage member 30 with fastening members, commonly designated at 104, each of which may be provided as an 8–32 by 1.375 inch (3.5 cm) socket head cap screw counterbored into the top surface 34 of carriage member 30. Each of fastening members 104 is shown as being maintained in a generally vertical alignment with an associated position guide bushing, commonly designated at 106, and to extend through carriage member 30 and a guide slot 70 guide into a threaded engagement with a corresponding guide member 102. In such an arrangement, each of guide members 102 is made to be slidably movable within a guide channel 100 for movement with carriage member 30 along longitudinal axis 14 (FIG. 1).

As it is anticipated that examination chair 10 will be used on carpeted surfaces and the like, there is presented the hazard that carpet fibers and the like may work to foul guide channels 100 and guide slots 70, thereby restricting the free movement of carriage member 30. Accordingly, as is shown at 110a–b in FIG. 1, guide slots 70 may be inwardly spaced from the outer periphery of base member 12 to define flanged regions protecting the guide slots and channels from the ingress of fibrous material or the like. The described inward spacing of the guide slots 70 also provides added load bearing support. For sealing each of guide channels 100a and 100b, a corresponding cover, 112a–b, is providing forming a continuous lower surface 22 on base member 12.

As it is further anticipated that base member 12 may not necessarily be secured to the floor surface, lower surface 22 thereof may be provided, as is shown at 120 in FIGS. 2–7, with a covering layer having a coefficient of static friction selected as effective to delimit the movement of base member 12 as carriage member 30 is moved along longitudinal axis 14 (FIG. 1) thereof. Covering layer 120 preferably is provided as a anti-skid, ribbed material formed of a polymeric material such as an elastomeric vinyl or the like which is oriented with its ribs extending generally perpendicular to longitudinal axis 14.

Figure 6:
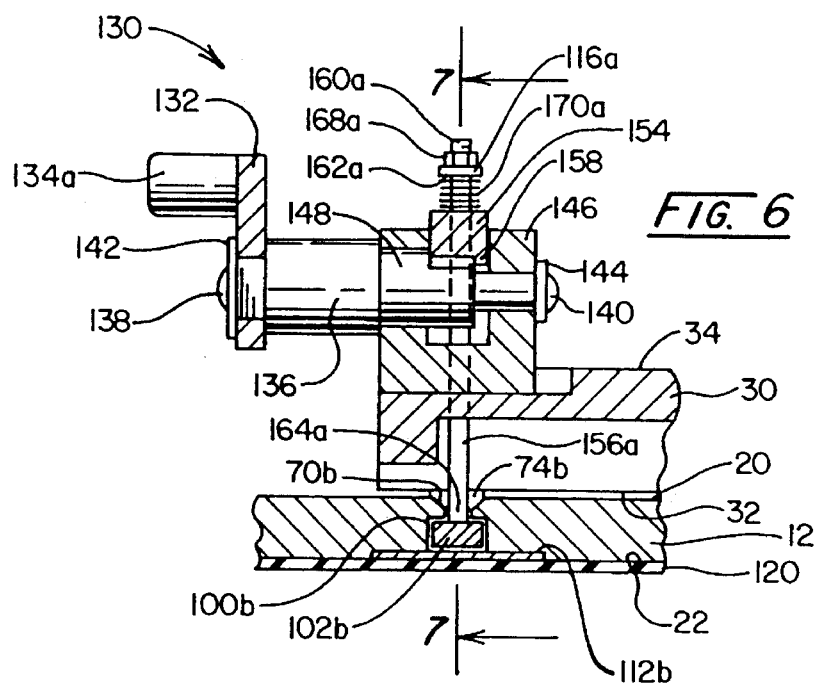
FIG. 6 is a cross-sectional view taken through line 6—6 of FIG. 2 showing in enhanced detail the locking assembly of the examination chair of FIG. 1.

Continuing with particular reference to FIGS. 6 and 7 in conjunction with FIGS. 1 and 2, a preferred arrangement of a locking assembly is shown at 130 for releasably locking carriage member 30 in its forward and rearward orientations. As may be seen in the figures, locking assembly 130 may be provided as including a hand or foot-operable actuator, 132, having a pair of associated lugs, 134a–b. Actuator 132 is connected to a shaft, 136, pivotally mounted with screws 138 and 140 and washers 142 and 144 on carriage member 30 within a generally U-shaped mounting block, 146. Shaft 136 extends within mounting block 146 to a bossed portion, 148, formed as having a first and second camming surface, represented at 150 and 152, respectively.

A cam follower member, 154, is connected via a pair of elongate coupling members, 156a and 156b, to at least one of guide members 102 which, for illustrative purposes, is shown as guide member 102b. Follower member 154 may be formed for stability as having a central U-shaped extension, partially shown at 158 in FIG. 6, configured to receive shaft 136. Each of coupling members 156 are mounted to extend slidably through follower member 154 and mounting block 146 from a threaded first end, 160a–b, having a bearing surface, 162a–b, to a second end, 164a–b, threadably engaged with guide member 102b. Each bearing surface 162 may be provided as a washer, 166a–b, secured to a corresponding coupling member with a nut, 168a–b.

With the arrangement shown, follower member 154 is movable by the pivoting of and actuator 132 and shaft 136 from a first position supported on first camming surface 150 disposing guide member 102b in a freely slidable orientation within guide channel 100b, to a second position supported on second camming surface 152 disposing guide member 102b in an abutting orientation within guide channel 100b. Such orientation, it will be appreciated, is effective to lock carriage member 30 in a fixed position with respect to base member 12.

Figure 8:
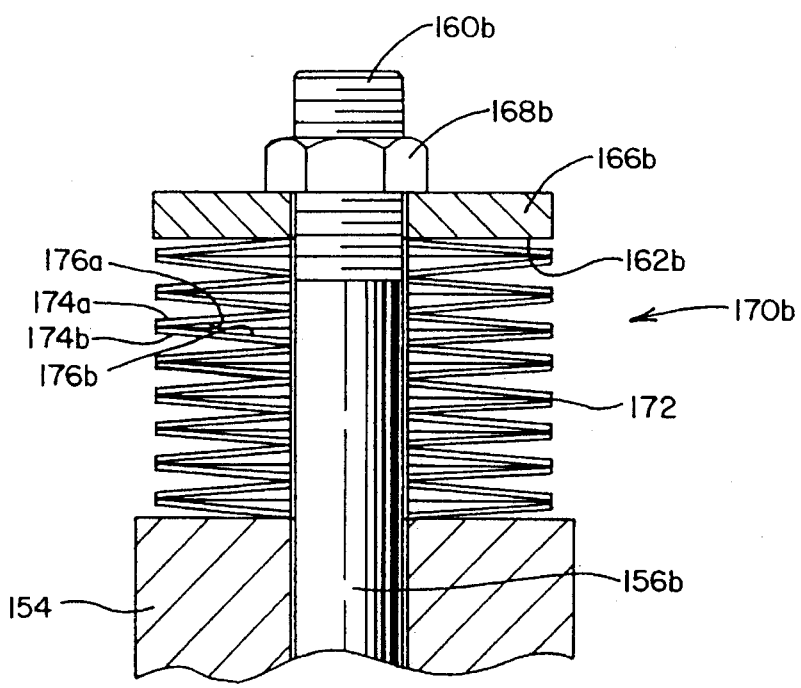
FIG. 8 is a cross-sectional view taken through line 8—8 of FIG. 7 showing a biasing assembly of the locking assembly of FIG. 7 in enhanced detail.

For normally biasing follower member 154 against bossed portion 148 of shaft 36, a biasing assembly, shown generally at 170a–b, may be interposed between each bearing surface 162 and follower member 154. In this regard, biasing assemblies 170 are provided to be compressible into a corresponding bearing surface 162 by the movement of follower member 154 disposing guide member 102b into its described abutting orientation with guide channel 70b locking carriage member 30 in a fixed position. Referring to FIG. 8, biasing assembly 170b is shown in enhanced detail to include a compressible spring member, shown generally at 172 to be coaxially received on coupling member 156b. Although spring member 172 may be provided as a helical spring, it is preferred for wear and performance considerations that spring member 172 be comprised of a compressible arrangement of at least a pair and, preferably, several pairs of beveled washers, two of which are shown at 174a and 174b. Each of washers 174 is formed as having a concave surface, 176a, disposed opposing a corresponding concave surface, 176b, of another washer 174. Such an assembly, it will be appreciated, provides a compressible arrangement effecting the noted biasing of follower member 154.

Returning to FIGS. 1 and 2, a forward stop member, 180, is shown to be mounted with screws 182a and 182b to the upper surface 20 of base member 12 at the forward end 16 thereof. As is detailed in FIG. 4, forward stop member 180 is configured to abuttingly engage a forward surface 184 of carriage member 30 disposing seat member 36 at its forward position spacing, as is shown in FIG. 9, a seated patient at the predetermined distance from an associated eye examination target. The abutting engagement effected between carriage member 30 and forward stop member 180 additionally delimits the travel of carriage member 30 beyond the extent of slots 70, thereby maintaining carriage member 30 positionally on base member 12. Likewise, a rearward stop member, 190, is mounted with screws 192a–b to the upper surface 20 of base member 12 at the rearward end 18 thereof to, as is shown in FIG. 10, abuttingly engage carriage member 30 disposing seat member 36 at its rearward position providing access to the associated instrument stand by a patient in a wheel chair positioned at the predetermined distance from the eye examination target. Thus, by virtue of forward and rearward stop members 180 and 190, examination chair 10 is made to be self-positioning with respect to the disposition of seat member 36 (FIGS. 9 and 10) at its calibrated forward and rearward positions.

Referring now to FIGS. 9 and 10, next considered is the methodology involved in conjunction with the present invention for providing access by a patient in a wheel chair to an ophthalmic instrument stand having an associated examination chair. Looking initially to FIG. 9, an instrument stand is shown at 200 as having a control panel, 202, and a movable arm, 204, extending therefrom on which is mounted an ophthalmic refractor, 206, configured to be placed confronting the eyes of the patient being examined. Additionally mounted on stand 200 may be an overhead light, 208, and any number of ophthalmic instruments, such as a keratometer, 210, and a slit lamp, 212, with corresponding support arms 214 and 216. A holder (not shown) for such hand-held diagnostic instruments as an ophthalmoscope and a retinoscope also may be provided. Indeed, the facile provision of wheel chair access to all of the eye examination instruments needed for a complete eye examination is specifically seen as a precept of the present invention.

Instrument stand 200 further is shown to be associated with examination chair 10 of the present invention, now illustrated as including seat member 36. As is illustrated in FIG. 9, carriage member 30 is locked with assembly 130 in a forward orientation abutting forward stop member 180 to dispose seat member 36 in a forward position for spacing a seated, ambulatory patient (not shown) a predetermined distance, represented at 220, from an associated eye examination target such as an eye chart, 222, or the like. In such position, examination chair 10 may readily receive the ambulatory patient for examination.

Looking next to FIG. 10, carriage member 30 is shown as having been translated rearwardly along base member 12 from the forward end 16 to the rearward end 18 thereof, and having been locked into a rearward orientation disposing seat member 36 of examination chair 10 in a rearward position providing access to instrument stand 200 by a disabled patient, 230, confined to a wheel chair, 240. Wheel chair 240 is shown generally as having a pair of rear wheels, 242, and a pair of smaller diameter front wheels, 244, and is depicted as having been moved rearwardly over the base member 12 of examination chair 10 with the rear wheels 242 thereof being received on the upper surface 20 of base member 12.

Looking momentarily to FIG. 1, it will be appreciated that flanged regions 110a and 110b have a widthwise extent providing at least an 18 inch (45.7 cm) track for receiving rear wheels 242 of wheel chair 240. Advantageously, such track also may accommodate the narrower wheel spans of children's chairs or the like. For other non-standard chairs such as custom chairs, however, it will be appreciated that one or both of rear wheels 242 thereof may be rolled as straddling base member 12 should the chair have a wheel span greater than the widthwise extent of base member 12.

Returning to FIG. 10, once moved rearwardly over base member 12, wheel chair 240 may be positioned at the forward position spacing patient 230 the predetermined distance 220 from eye chart 222. In this regard, it may be seen that an abutting engagement may be effected between the rear wheels 242 of wheel chair 240 and a portion of examination chair 10 such as rest portion 46 of seat member 36. Such an engagement advantageously may be designed as delimiting the rearward movement of wheel chair 240 positioning the chair effective to space patient 230 therein at predetermined distance 220 from eye chart 222. Looking additionally to FIG. 1, the forward end 16 of base member 12 is shown to be preferably configured as having a generally trapezoidal profile defined by the angles designated "θ," which may be about 30°. So configured, forward end 16 presents a pair of forwardly disposed surfaces, 260a-b, for confronting and abuttingly engaging the front wheels 244 (FIG. 10) of wheel chair 240. Such confrontation may further assist in the positioning of wheel chair 240 to space patient 230 at predetermined distance 220 from eye chart 222. Additionally, and as is shown by the angle designated "β" in FIG. 2, surfaces 260a-b may be configured as being angled at about 30° to provided a rearwardly inclined surface facilitating the movement of rear wheels 242 of wheel chair 240 onto upper surface 20 of base member 12.

Thus, a methodology is described in connection with FIGS. 9 and 10 which provides efficient wheel chair access to instrument stand 200 in a minimum amount of space and time, and which allows the disabled patient 230 to remain seated in wheel chair 240. It will be appreciated that, by virtue of the present invention, examination chair 10 may be moved and disable patient 240 may be properly positioned with considerable speed. As most providers examine patients only according to a predetermined exam schedule which affords each patient only a certain amount of exam time, and as the provider may not be informed beforehand as to the disability of the particular patient to be examined next according to the schedule, the ability to quickly accommodate for that disability will be seen to be especially desirable.

Referring next to FIG. 11, an alternative embodiment of lower base member 12 is shown at 12' as having forward end 16' with a more exaggerated trapezoidal profile. Such profile is defined by the angles θ, now shown to be 10° to 15°, and has a median widthwise extent, "l," of about 20.5 inches (52 cm). So configured, a predominate portion of the forward extent of base member 12' is receivable between the 20–22 inch (51–56 cm) wheel spans of most wheel chairs, and thereby obviates, for most patients, any need to move the rear wheels of the chair rearwardly over the top surface 20' of base member 12'. With the wheel chair straddling base member 12', the chair may be moved rearwardly into the abutting engagement described in connection with FIG. 10 for its positioning at the forward position spacing the patient at a predetermined distance 200 from eye chart 222. It has been observed that the tapered configuration of base member 12' advantageously functions as a guide maintaining a generally straight alignment as the wheel chair is moved rearwardly over base member 12'. Alternatively, where base member 12' is utilized in conjunction with custom or child chairs having wheel spans smaller than standard, the rear wheels thereof may be received on the upper surface 20' in the manner which was described in connection with FIG. 10 for base member 12.

As is shown at 300, at least a portion of the outer periphery of lower base member 12' preferably is configured to provide a rearwardly inclined surface presented to confront the wheel chair. Looking to FIG. 12, rearwardly inclined surface 300, which also may be incorporated into base member 12 (FIG. 1), is shown to include an upstanding outer portion, 302, and an inclined inner portion, 304. Inner portion 304 defines an angle, β, with the vertical which preferably is about 30°. For instances in which the rear wheels of the wheel chair are moved rearwardly over base member 12 or 12' as being received on the upper surface 20 or 20' thereof, inclined surface 300 functions as a ramp which facilitates the loading of the chair onto the upper surface. For either application, the lowered profile of inclined surface 300 provides an anti-tripping feature for an added measure of safety for the practitioner, the ambulatory patient, and any other person working around the base plate.

It is anticipated that certain changes may be made in the present invention without departing from the precepts herein involved. Accordingly, it is intended that all matter contained in the foregoing description shall be interpreted as illustrative and not in a limiting sense.

What is claimed:

1. An ophthalmic examination chair normally disposed at a forward position for use in conjunction with an instrument stand and movable therefrom to provide access at said forward position for a wheelchair comprising:

a seat member configured to receive a seated patient at said forward position;

a carriage member having a bottom portion and a top portion supporting said seat member thereon, and including at least a pair of spaced apart guide rollers mounted at said bottom portion, for supporting and guiding the movement of said seat member, a base member extending along a longitudinal axis between a forward end and a rearward end, having an upper and a lower surface, a pair of spaced apart guide slots formed through said upper surface, extending in generally parallel relationship with said longitudinal axis and having side surfaces for receiving and movably supporting said carriage member guide rollers for moving said carriage and supported seat member into and a predetermined distance away from said forward position, said predetermined distance being selected to provide access for said wheelchair at said forward position, including a pair of spaced-apart guide channels, extending beneath in registry and open communication with a corresponding one of said guide slots, and a pair of guide members, each being slideably located within a said guide channel and fastened to said carriage member for retaining said carriage member upon said base member; and a locking assembly for releasably locking said carriage member upon said base member.

2. The examination chair of claim 1 further comprising a forward stop member mounted to the upper surface of said base member at the forward end thereof, said stop member configured to abuttingly engage said carriage member to dispose said seat member at said forward position.

3. The examination chair of claim 1 further comprising a rearward stop member mounted to the upper surface of said base member at the rearward end thereof, said stop member configured to abuttingly engage said carriage member to dispose said seat member adjacent said base member rearward end.

4. The examination chair of claim 1 wherein:

said side surfaces are inwardly sloping and extend intermediate the forward and rearward ends of said base member generally parallel to said longitudinal axis; and each of said guide rollers is vertically mounted to the bottom surface of said carriage member as having an axis of rotation generally parallel thereto, the outer periphery of each of said guide rollers having a profile configured to be received on the said side surfaces of said corresponding one of said guide slots.

5. The examination chair of claim 1 wherein said bottom portion of said carriage member is formed as having at least a pair of recesses each configured to receive a portion of a corresponding one of said rollers therewithin, said chair further comprising at least a pair of axles each having a first end supported within said carriage member and extending across a corresponding one of said recesses to second end supported within said carriage member, each of said axles rotatably supporting a corresponding one of said rollers intermediate said first and said second end.

6. The examination chair of claim 5 wherein each of said axles extends from said second end to a threaded terminal region fastened within a corresponding threaded aperture formed into said carriage member.

7. The examination chair of claim 1 wherein said locking assembly comprises:

a shaft pivotally mounted on said carriage member and extending to a bossed portion formed as having a first and second camming surface; and a follower member connected to at least one of said guide members and movable by the pivoting of said shaft from a first position supported on said first camming surface disposing said one of said guide members in a freely slidable orientation within said guide channel to a second position supported on said second camming surface disposing said one of said guide members in all abutting orientation with said guide channel locking said carriage member in a fixed position with respect to said base member.

8. The examination chair of claim 7 wherein said locking assembly further comprises:

at least one elongate coupling member extending slidably through said follower member from a first end having a bearing surface to a second end fastened to said one of said guide members; and a biasing assembly interposed between said bearing surface and said follower member, said biasing assembly normally biasing said follower member against said bossed portion of said shaft and being compressible into said bearing surface by the movement of said follower member disposing said one of said guide members in said abutting orientation with said guide channel.

9. The examination chair of claim 8 wherein said biasing assembly includes a compressible spring member coaxially received on said coupling member.

10. The examination chair of claim 9 wherein said spring member is formed of at least a pair of beveled washers, each of said beveled washers having a concave surface disposed opposing a corresponding concave surface of another said washer.

11. The examination chair of claim 1 wherein the lower surface of said base member is provided with a covering layer having a coefficient of static friction selected as effective to delimit any movement of said base member as said carriage member is moved along the longitudinal axis thereof.

12. The examination chair of claim 11 wherein said covering layer is formed of a polymeric material having a plurality of ribs oriented to extend generally perpendicular to the longitudinal axis of said base member.

13. The examination chair of claim 1 wherein said base member upper surface is formed as having a widthwise extent configured to receive the rear wheels of the wheel chair thereon.

14. The examination chair of claim 13 wherein said base member forward end is formed as having a generally trapezoidal profile forming a pair of confrontation surfaces for abuttingly engaging the front wheels of the wheel chair.

15. The examination chair of claim 14 wherein said confrontation surfaces are inclined rearwardly for facilitating the movement of the rear wheels of the wheel chair onto said base member upper surface.

16. The examination chair of claim 3 wherein said examination chair is positioned to abuttingly engage the wheel chair for its positioning effective to space the patient therein at said predetermined distance from the eye examination target when said carriage member is in abuttable engagement with said rearward stop member.

17. The examination chair of claim 1 wherein said base member forward end is formed as having a generally trapezoidal profile configured to be received between the rear wheels of the wheel chair.

18. The examination chair of claim 1 wherein said lower base member is defined as having an outer periphery, at least a portion of which is formed as a rearwardly inclined surface.

19. The examination chair of claim 1 in which said predetermined distance is about 20 inches.

20. A method of providing access by patient in a wheel chair to an ophthalmic instrument stand having an associated examination chair and eye examination target, said method comprising the steps of:

(a) providing said examination chair as comprising:

a seat member configured to receive a seated patient and movable from a forward position spacing the seated patient a predetermined distance from the eye examination target;

a lower base member extending along a longitudinal axis between a forward end and a rearward end and having an upper and a lower surface; and an upper carriage member having a bottom surface and a top surface supporting said seat member thereon, said carriage member being supposed on the upper surface of said base member for movement between the forward and the rearward end thereof along said longitudinal axis to position said seat member at said forward position and at a rearward position for providing access to the instrument stand by the patient in a wheel chair;

(b) moving said carriage member of said examination chair rearwardly along the longitudinal axis of said base member to move said seat member from said forward position to said rearward position;

(c) moving the wheel chair rearwardly over said base member of said examination chair; and (d) positioning the wheel chair to space the patient therein at said predetermined distance from the eye examination target.

21. The method of claim 20 wherein the wheel chair is moved rearwardly over said base member of said examination chair into an abutting engagement therewith positioning the wheel chair effective to space the patient therein at said predetermined distance from the eye examination target.

22. The method of claim 20 wherein the wheel chair is moved rearwardly over said base member of said examination chair with the rear wheels of the wheel chair being received on the upper surface of said base member.

23. The method of claim 20 wherein said examination chair is provided as further comprising a locking assembly for releasably locking said carriage member in a forward orientation disposing said seat member at said forward position and in a rearward orientation disposing said seat member at said rearward position, said method further comprising the step after step (b) of locking said carriage member in said rearward orientation.

* * * * *